US007040549B2

(12) United States Patent
Ivri et al.

(10) Patent No.: US 7,040,549 B2
(45) **Date of Patent: *May 9, 2006**

(54) SYSTEMS AND METHODS FOR CONTROLLING FLUID FEED TO AN AEROSOL GENERATOR

(75) Inventors: Yehuda Ivri, Irvine, CA (US); Markus Flierl, Sunnyvale, CA (US)

(73) Assignee: Aerogen, Inc., Mountain View, CA (US)

(*) Notice: Subject to any disclaimer, the term of this patent is extended or adjusted under 35 U.S.C. 154(b) by 65 days.

This patent is subject to a terminal disclaimer.

(21) Appl. No.: 10/394,512

(22) Filed: Mar. 21, 2003

(65) Prior Publication Data

US 2004/0004133 A1 Jan. 8, 2004

Related U.S. Application Data

(63) Continuation of application No. 09/678,410, filed on Oct. 2, 2000, now Pat. No. 6,540,154, which is a continuation-in-part of application No. 09/318,552, filed on May 27, 1999, now Pat. No. 6,540,153, which is a continuation of application No. 08/417,311, filed on Apr. 5, 1995, now Pat. No. 5,938,117, which is a continuation-in-part of application No. 08/163,850, filed on Dec. 7, 1993, now Pat. No. 6,629,646, which is a continuation-in-part of application No. 07/726,777, filed on Jul. 8, 1991, now abandoned, which is a continuation-in-part of application No. 07/691,584, filed on Apr. 24, 1991, now Pat. No. 5,164,740.

(51) Int. Cl.
*B05B 1/08* (2006.01)

(52) U.S. Cl. .................. 239/102.2; 239/338; 239/552; 128/200.16

(58) Field of Classification Search .................... 239/4, 239/11, 102.1, 102.2, 338, 552; 128/200.16
See application file for complete search history.

(56) References Cited

U.S. PATENT DOCUMENTS

| | | | |
|---|---|---|---|
| 550,315 | A | 11/1895 | Allen |
| 809,159 | A | 1/1906 | Willis et al. |
| 1,680,616 | A | 8/1928 | Horst |
| 2,022,520 | A | 11/1935 | Philbrick |
| 2,101,304 | A | 12/1937 | Wright |
| 2,158,615 | A | 5/1939 | Wright |
| 2,187,528 | A | 1/1940 | Wing |
| 2,223,541 | A | 12/1940 | Baker |

(Continued)

FOREIGN PATENT DOCUMENTS

| | | |
|---|---|---|
| CH | 477 855 | 9/1969 |

(Continued)

OTHER PUBLICATIONS

Abys, J.A. et al., “Annealing Behavior of Palladium-Nickel Alloy Electrodeposits,” Plating and Surface Finishing, Aug. 1996, pp. 1-7.

(Continued)

*Primary Examiner*—Steven J. Ganey
(74) *Attorney, Agent, or Firm*—Townsend and Townsend and Crew LLP

(57) ABSTRACT

A method for controlling the supply of liquid to an aerosol generator comprises operating a liquid supply system to supply a liquid to a vibratable aperture plate of an aerosol generator which senses an amount of liquid adhering to the vibratable aperture plate, and controls operation of the liquid supply system to adjust the amount of liquid adhering to the vibratable aperture plate.

29 Claims, 8 Drawing Sheets

U.S. PATENT DOCUMENTS

| | | |
|---|---|---|
| 2,266,706 A | 12/1941 | Fox et al. |
| 2,283,333 A | 5/1942 | Martin |
| 2,292,381 A | 8/1942 | Klagges |
| 2,360,297 A | 10/1944 | Wing |
| 2,375,770 A | 5/1945 | Dahlberg |
| 2,383,098 A | 8/1945 | Wheaton |
| 2,404,063 A | 7/1946 | Healy |
| 2,430,023 A | 11/1947 | Longmaid |
| 2,474,996 A | 7/1949 | Wallis |
| 2,512,004 A | 6/1950 | Wing |
| 2,521,657 A | 9/1950 | Severy |
| 2,681,041 A | 6/1954 | Zodtner et al. |
| 2,705,007 A | 3/1955 | Gerber |
| 2,735,427 A | 2/1956 | Sullivan |
| 2,764,946 A | 10/1956 | Henderson |
| 2,764,979 A | 10/1956 | Henderson |
| 2,779,623 A | 1/1957 | Eisenkraft |
| 2,935,970 A | 5/1960 | Morse et al. |
| 3,103,310 A | 9/1963 | Lang |
| 3,325,031 A | 6/1967 | Singier |
| 3,411,854 A | 11/1968 | Rosler et al. |
| 3,515,348 A | 6/1970 | Coffman, Jr. |
| 3,550,864 A | 12/1970 | East |
| 3,558,052 A | 1/1971 | Dunn |
| 3,561,444 A | 2/1971 | Boucher |
| 3,563,415 A | 2/1971 | Ogle |
| 3,680,954 A | 8/1972 | Frank |
| 3,719,328 A | 3/1973 | Hindman |
| 3,738,574 A | 6/1973 | Guntersdorfer et al. |
| 3,771,982 A | 11/1973 | Dobo |
| 3,790,079 A | 2/1974 | Berglund et al. |
| 3,804,329 A | 4/1974 | Martner |
| 3,812,854 A | 5/1974 | Michaels et al. |
| 3,838,686 A | 10/1974 | Szekely |
| 3,842,833 A | 10/1974 | Ogle |
| 3,865,106 A | 2/1975 | Palush |
| 3,903,884 A | 9/1975 | Huston et al. |
| 3,906,950 A | 9/1975 | Cocozza |
| 3,908,654 A | 9/1975 | Lhoest et al. |
| 3,950,760 A | 4/1976 | Rauch et al. |
| 3,951,313 A | 4/1976 | Coniglione |
| 3,958,249 A | 5/1976 | DeMaine et al. |
| 3,970,250 A | 7/1976 | Drews |
| 3,983,740 A | 10/1976 | Danel |
| 3,993,223 A | 11/1976 | Welker, III et al. |
| 4,005,435 A | 1/1977 | Lundquist et al. |
| 4,030,492 A | 6/1977 | Simburner |
| 4,052,986 A | 10/1977 | Scaife |
| 4,059,384 A | 11/1977 | Holland et al. |
| D246,574 S | 12/1977 | Meierhoefer |
| 4,076,021 A | 2/1978 | Thompson |
| 4,083,368 A | 4/1978 | Freezer |
| 4,094,317 A | 6/1978 | Wasnich |
| 4,101,041 A | 7/1978 | Mauro, Jr. et al. |
| 4,106,503 A | 8/1978 | Rsenthal et al. |
| 4,109,174 A | 8/1978 | Hodgson |
| 4,113,809 A | 9/1978 | Abair et al. |
| D249,958 S | 10/1978 | Meierhoefer |
| 4,119,096 A | 10/1978 | Drews |
| 4,121,583 A | 10/1978 | Chen |
| 4,159,803 A | 7/1979 | Cameto et al. |
| 4,207,990 A | 6/1980 | Weiler et al. |
| 4,210,155 A | 7/1980 | Grimes |
| 4,226,236 A | 10/1980 | Genese |
| 4,240,081 A | 12/1980 | Devitt |
| 4,240,417 A | 12/1980 | Holever |
| 4,248,227 A | 2/1981 | Thomas |
| 4,261,512 A | 4/1981 | Zierenberg |
| D259,213 S | 5/1981 | Pagels |
| 4,268,460 A | 5/1981 | Boiarski et al. |
| 4,294,407 A | 10/1981 | Reichl et al. |
| 4,298,045 A | 11/1981 | Weiler et al. |
| 4,299,784 A | 11/1981 | Hense |
| 4,300,546 A | 11/1981 | Kruber |
| 4,301,093 A | 11/1981 | Eck |
| 4,319,155 A | 3/1982 | Makai et al. |
| 4,334,531 A | 6/1982 | Reichl et al. |
| 4,336,544 A | 6/1982 | Donald et al. |
| 4,338,576 A | 7/1982 | Takahashi et al. |
| 4,368,476 A | 1/1983 | Uehara et al. |
| 4,368,850 A | 1/1983 | Szekely |
| 4,374,707 A | 2/1983 | Pollack |
| 4,389,071 A | 6/1983 | Johnson, Jr. et al. |
| 4,408,719 A | 10/1983 | Last |
| 4,428,802 A | 1/1984 | Kanai et al. |
| 4,431,136 A | 2/1984 | Janner et al. |
| 4,454,877 A | 6/1984 | Miller et al. |
| 4,465,234 A | 8/1984 | Maehara et al. |
| 4,474,251 A | 10/1984 | Johnson, Jr. |
| 4,474,326 A | 10/1984 | Takahashi |
| 4,475,113 A | 10/1984 | Lee et al. |
| 4,479,609 A | 10/1984 | Maeda et al. |
| 4,512,341 A | 4/1985 | Lester |
| 4,530,464 A | 7/1985 | Yamamoto et al. |
| 4,533,082 A * | 8/1985 | Maehara et al. ......... 239/102.2 |
| 4,539,575 A | 9/1985 | Nilsson |
| 4,544,933 A | 10/1985 | Heinzl |
| 4,546,361 A | 10/1985 | Brescia et al. |
| 4,550,325 A | 10/1985 | Viola |
| 4,566,452 A | 1/1986 | Farr |
| 4,591,883 A | 5/1986 | Isayama |
| 4,593,291 A | 6/1986 | Howkins |
| 4,605,167 A | 8/1986 | Maehara |
| 4,613,326 A | 9/1986 | Szwarc |
| 4,620,201 A | 10/1986 | Heinzl et al. |
| 4,628,890 A | 12/1986 | Freeman |
| 4,632,311 A | 12/1986 | Nakane et al. |
| 4,658,269 A | 4/1987 | Rezanka |
| 4,659,014 A | 4/1987 | Soth et al. |
| 4,677,975 A | 7/1987 | Edgar et al. |
| 4,678,680 A | 7/1987 | Abowitz |
| 4,679,551 A | 7/1987 | Anthony |
| 4,681,264 A | 7/1987 | Johnson, Jr. |
| 4,693,853 A | 9/1987 | Falb et al. |
| 4,702,418 A * | 10/1987 | Carter et al. ................... 239/4 |
| 4,722,906 A | 2/1988 | Guire |
| 4,753,579 A | 6/1988 | Murphy |
| 4,790,479 A | 12/1988 | Matsumoto et al. |
| 4,793,339 A | 12/1988 | Matsumoto et al. |
| 4,796,807 A | 1/1989 | Bendig et al. |
| 4,799,622 A | 1/1989 | Ishikawa et al. |
| 4,805,609 A | 2/1989 | Roberts et al. |
| 4,819,629 A | 4/1989 | Jonson |
| 4,819,834 A | 4/1989 | Thiel |
| 4,826,080 A | 5/1989 | Ganser |
| 4,826,759 A | 5/1989 | Guire et al. |
| 4,828,886 A | 5/1989 | Hieber |
| 4,843,445 A | 6/1989 | Stemme |
| 4,849,303 A | 7/1989 | Graham et al. |
| 4,850,534 A | 7/1989 | Takahashi et al. |
| 4,865,006 A | 9/1989 | Nogi et al. |
| 4,871,489 A | 10/1989 | Ketcham |
| 4,872,553 A | 10/1989 | Suzuki et al. |
| 4,877,989 A | 10/1989 | Drews et al. |
| 4,888,516 A | 12/1989 | Daeges et al. |
| 4,922,901 A | 5/1990 | Brooks et al. |
| 4,926,915 A | 5/1990 | Deussen et al. |
| 4,934,358 A | 6/1990 | Nilsson et al. |
| 4,954,225 A | 9/1990 | Bakewell |
| 4,957,239 A | 9/1990 | Tempelman |
| 4,964,521 A | 10/1990 | Wieland et al. |
| D312,209 S | 11/1990 | Morrow et al. |
| 4,968,299 A | 11/1990 | Ahlstrand et al. |
| 4,971,665 A | 11/1990 | Sexton |

| | | | | | |
|---|---|---|---|---|---|
| 4,973,493 A | 11/1990 | Guire | 5,415,161 A | 5/1995 | Ryder |
| 4,976,259 A | 12/1990 | Higson et al. | 5,419,315 A | 5/1995 | Rubsamen |
| 4,979,959 A | 12/1990 | Guire | 5,426,458 A | 6/1995 | Wenzel et al. |
| 4,994,043 A | 2/1991 | Ysebaert | 5,431,155 A | 7/1995 | Marelli |
| 5,002,048 A | 3/1991 | Makiej, Jr. | 5,435,282 A | 7/1995 | Haber et al. |
| 5,002,582 A | 3/1991 | Guire et al. | 5,435,297 A | 7/1995 | Klein |
| 5,007,419 A | 4/1991 | Weinstein et al. | 5,437,267 A | 8/1995 | Weinstein et al. |
| 5,016,024 A | 5/1991 | Lam et al. | 5,445,141 A | 8/1995 | Kee et al. |
| 5,021,701 A | 6/1991 | Takahashi et al. | D362,390 S | 9/1995 | Weiler |
| 5,022,587 A | 6/1991 | Hochstein | 5,449,502 A | 9/1995 | Igusa et al. |
| 5,024,733 A | 6/1991 | Abys et al. | 5,452,711 A | 9/1995 | Gault |
| 5,046,627 A | 9/1991 | Hansen | 5,458,135 A | 10/1995 | Patton et al. |
| 5,062,419 A | 11/1991 | Rider | 5,458,289 A | 10/1995 | Cater |
| 5,063,396 A | 11/1991 | Shiokawa et al. | 5,474,059 A | 12/1995 | Cooper |
| 5,063,922 A | 11/1991 | Häkkinen | 5,477,992 A | 12/1995 | Jinks et al. |
| 5,073,484 A | 12/1991 | Swanson et al. | 5,479,920 A | 1/1996 | Piper et al. |
| 5,076,266 A | 12/1991 | Babaev | 5,487,378 A * | 1/1996 | Robertson et al. ..... 128/200.16 |
| 5,080,093 A | 1/1992 | Raabe et al. | 5,489,266 A | 2/1996 | Grimard |
| 5,080,649 A | 1/1992 | Vetter | 5,497,944 A | 3/1996 | Weston et al. |
| 5,086,765 A | 2/1992 | Levine | D369,212 S | 4/1996 | Snell |
| 5,086,785 A * | 2/1992 | Gentile et al. .............. 338/210 | 5,511,726 A | 4/1996 | Greenspan et al. |
| 5,115,803 A | 5/1992 | Sioutas | 5,512,329 A | 4/1996 | Guire et al. |
| 5,115,971 A | 5/1992 | Greenspan et al. | 5,512,474 A | 4/1996 | Clapper et al. |
| D327,008 S | 6/1992 | Friedman | 5,515,841 A | 5/1996 | Robertson et al. |
| 5,122,116 A | 6/1992 | Kriesel et al. | 5,515,842 A | 5/1996 | Ramseyer et al. |
| 5,129,579 A | 7/1992 | Conte | 5,516,043 A | 5/1996 | Manna et al. |
| 5,134,993 A | 8/1992 | Van Der Linden et al. | 5,518,179 A | 5/1996 | Humberstone et al. |
| 5,139,016 A | 8/1992 | Waser | 5,529,055 A | 6/1996 | Gueret |
| 5,140,740 A * | 8/1992 | Weigelt ........................ 29/596 | 5,533,497 A | 7/1996 | Ryder |
| 5,147,073 A | 9/1992 | Cater | 5,542,410 A | 8/1996 | Goodman et al. |
| 5,152,456 A | 10/1992 | Ross et al. | 5,549,102 A | 8/1996 | Lintl et al. |
| 5,157,372 A * | 10/1992 | Langford .................... 338/211 | 5,560,837 A | 10/1996 | Trueba |
| 5,164,740 A * | 11/1992 | Ivri ........................ 346/139 C | 5,563,056 A | 10/1996 | Swan et al. |
| 5,169,029 A | 12/1992 | Behar et al. | D375,352 S | 11/1996 | Bologna |
| 5,170,782 A | 12/1992 | Kocinski | 5,579,757 A | 12/1996 | McMahon et al. |
| 5,180,482 A | 1/1993 | Abys et al. | 5,582,330 A | 12/1996 | Iba |
| 5,186,164 A | 2/1993 | Raghuprasad | 5,584,285 A | 12/1996 | Salter et al. |
| 5,186,166 A | 2/1993 | Riggs et al. | 5,586,550 A * | 12/1996 | Ivri et al. .............. 128/200.16 |
| 5,198,157 A | 3/1993 | Bechet | 5,588,166 A | 12/1996 | Burnett |
| 5,201,322 A | 4/1993 | Henry et al. | 5,601,077 A | 2/1997 | Imbert |
| 5,213,860 A | 5/1993 | Laing | 5,609,798 A | 3/1997 | Liu et al. |
| 5,217,148 A | 6/1993 | Cater | 5,632,878 A | 5/1997 | Kitano |
| 5,217,492 A | 6/1993 | Guire et al. | 5,635,096 A | 6/1997 | Singer et al. |
| 5,227,168 A | 7/1993 | Chvapil | 5,637,460 A | 6/1997 | Swan et al. |
| 5,230,496 A | 7/1993 | Shillington et al. | 5,647,349 A | 7/1997 | Ohki et al. |
| 5,245,995 A | 9/1993 | Sullivan et al. | 5,653,227 A | 8/1997 | Barnes et al. |
| 5,248,087 A | 9/1993 | Dressler | 5,654,007 A | 8/1997 | Johnson et al. |
| 5,258,041 A | 11/1993 | Guire et al. | 5,654,162 A | 8/1997 | Guire et al. |
| 5,261,601 A * | 11/1993 | Ross et al. ............. 128/200.16 | 5,654,460 A | 8/1997 | Rong |
| 5,263,992 A | 11/1993 | Guire | 5,657,926 A | 8/1997 | Toda |
| 5,279,568 A | 1/1994 | Cater | 5,660,166 A | 8/1997 | Lloyd |
| 5,297,734 A | 3/1994 | Toda | 5,664,557 A | 9/1997 | Makiej, Jr. |
| 5,299,739 A | 4/1994 | Takahashi et al. | 5,664,706 A | 9/1997 | Cater |
| 5,303,854 A | 4/1994 | Cater | 5,665,068 A | 9/1997 | Takamura |
| 5,309,135 A * | 5/1994 | Langford .................... 338/211 | 5,666,946 A | 9/1997 | Langenback |
| 5,312,281 A | 5/1994 | Takahashi et al. | 5,670,999 A | 9/1997 | Takeuchi et al. |
| 5,313,955 A | 5/1994 | Rodder | 5,685,491 A | 11/1997 | Marks et al. |
| 5,319,971 A | 6/1994 | Osswald et al. | 5,692,644 A | 12/1997 | Gueret |
| 5,320,603 A | 6/1994 | Vetter et al. | 5,707,818 A | 1/1998 | Chudzik et al. |
| 5,322,057 A | 6/1994 | Raabe et al. | 5,709,202 A | 1/1998 | Lloyd et al. |
| 5,342,011 A | 8/1994 | Short | 5,714,360 A | 2/1998 | Swan et al. |
| 5,342,504 A | 8/1994 | Hirano et al. | 5,714,551 A | 2/1998 | Bezwada et al. |
| 5,347,998 A | 9/1994 | Hodson et al. | 5,718,222 A | 2/1998 | Lloyd et al. |
| 5,348,189 A | 9/1994 | Cater | D392,184 S | 3/1998 | Weiler |
| 5,350,116 A | 9/1994 | Cater | 5,724,957 A | 3/1998 | Rubsamen et al. |
| 5,355,872 A | 10/1994 | Riggs et al. | 5,744,515 A | 4/1998 | Clapper |
| 5,357,946 A | 10/1994 | Kee et al. | 5,752,502 A | 5/1998 | King |
| 5,372,126 A | 12/1994 | Blau | 5,755,218 A | 5/1998 | Johansson et al. |
| 5,383,906 A | 1/1995 | Burchett et al. | 5,758,637 A * | 6/1998 | Ivri et al. .............. 128/200.16 |
| 5,388,571 A | 2/1995 | Roberts et al. | 5,775,506 A | 7/1998 | Grabenkort |
| 5,392,768 A | 2/1995 | Johansson et al. | 5,788,665 A | 8/1998 | Sekins |
| 5,396,883 A | 3/1995 | Knupp et al. | 5,788,819 A | 8/1998 | Onishi et al. |
| 5,414,075 A | 5/1995 | Swan et al. | 5,790,151 A | 8/1998 | Mills |

| | | |
|---|---|---|
| 5,810,004 A | 9/1998 | Ohki et al. |
| 5,819,730 A | 10/1998 | Stone et al. |
| 5,823,179 A | 10/1998 | Grychowski et al. |
| 5,823,428 A | 10/1998 | Humberstone et al. |
| 5,829,723 A | 11/1998 | Brunner et al. |
| 5,836,515 A | 11/1998 | Fonzes |
| 5,839,617 A | 11/1998 | Cater et al. |
| 5,842,468 A | 12/1998 | Denyer et al. |
| 5,865,171 A | 2/1999 | Cinquin |
| 5,878,900 A | 3/1999 | Hansen |
| 5,893,515 A | 4/1999 | Hahn et al. |
| 5,894,841 A | 4/1999 | Voges |
| 5,897,008 A | 4/1999 | Hansen |
| 5,910,698 A | 6/1999 | Yagi |
| 5,915,377 A | 6/1999 | Coffee |
| 5,918,637 A | 7/1999 | Fleischman |
| 5,925,019 A | 7/1999 | Ljungquist |
| 5,938,117 A | 8/1999 | Ivri |
| 5,950,619 A | 9/1999 | Van Der Linden et al. |
| 5,954,268 A | 9/1999 | Joshi et al. |
| 5,960,792 A | 10/1999 | Lloyd et al. |
| 5,964,417 A | 10/1999 | Amann et al. |
| 5,970,974 A | 10/1999 | Van Der Linden et al. |
| 5,976,344 A | 11/1999 | Abys et al. |
| 5,993,805 A | 11/1999 | Sutton et al. |
| 6,007,518 A | 12/1999 | Kriesel et al. |
| 6,012,450 A | 1/2000 | Rubsamen |
| 6,014,970 A * | 1/2000 | Ivri et al. ............... 128/200.16 |
| 6,026,809 A | 2/2000 | Abrams et al. |
| 6,032,665 A | 3/2000 | Psaros |
| 6,037,587 A | 3/2000 | Dowell et al. |
| 6,045,215 A | 4/2000 | Coulman |
| 6,045,874 A | 4/2000 | Himes |
| 6,047,818 A | 4/2000 | Warby et al. |
| 6,055,869 A | 5/2000 | Stemme et al. |
| 6,060,128 A | 5/2000 | Kim et al. |
| 6,062,212 A | 5/2000 | Davison et al. |
| 6,068,148 A | 5/2000 | Weiler |
| 6,085,740 A | 7/2000 | Ivri et al. |
| 6,096,011 A | 8/2000 | Trombley, III et al. |
| 6,105,877 A | 8/2000 | Coffee |
| 6,106,504 A | 8/2000 | Urrutia |
| 6,116,234 A | 9/2000 | Genova et al. |
| 6,123,413 A | 9/2000 | Agarwal et al. |
| 6,139,674 A | 10/2000 | Markham et al. |
| 6,142,146 A | 11/2000 | Abrams et al. |
| 6,145,963 A | 11/2000 | Pidwerbecki et al. |
| 6,146,915 A | 11/2000 | Pidwerbecki et al. |
| 6,152,130 A | 11/2000 | Abrams et al. |
| 6,155,676 A | 12/2000 | Etheridge et al. |
| 6,158,431 A | 12/2000 | Poole |
| 6,161,536 A | 12/2000 | Redmon et al. |
| 6,163,588 A | 12/2000 | Matsumoto et al. |
| 6,182,662 B1 | 2/2001 | McGhee |
| 6,186,141 B1 | 2/2001 | Pike et al. |
| 6,196,218 B1 | 3/2001 | Voges |
| 6,196,219 B1 | 3/2001 | Hess et al. |
| 6,205,999 B1 | 3/2001 | Ivri et al. |
| 6,216,916 B1 | 4/2001 | Maddox et al. |
| 6,223,746 B1 | 5/2001 | Jewett et al. |
| 6,235,177 B1 | 5/2001 | Borland et al. |
| 6,254,219 B1 | 7/2001 | Agarwal et al. |
| 6,270,473 B1 | 8/2001 | Schwebel |
| 6,273,342 B1 * | 8/2001 | Terada et al. ............ 239/102.2 |
| 6,318,640 B1 | 11/2001 | Coffee |
| 6,328,030 B1 | 12/2001 | Kidwell et al. |
| 6,328,033 B1 | 12/2001 | Avrahami |
| 6,341,732 B1 | 1/2002 | Martin et al. |
| 6,358,058 B1 | 3/2002 | Strupat et al. |
| 6,394,363 B1 | 5/2002 | Arnott et al. |
| 6,402,046 B1 | 6/2002 | Loser |
| 6,405,934 B1 | 6/2002 | Hess et al. |
| 6,427,682 B1 | 8/2002 | Klimowicz et al. |
| 6,443,146 B1 | 9/2002 | Voges |
| 6,443,366 B1 | 9/2002 | Hirota et al. |
| 6,467,476 B1 | 10/2002 | Ivri et al. |
| 6,530,370 B1 | 3/2003 | Heinonen |
| 6,540,153 B1 | 4/2003 | Ivri |
| 6,540,154 B1 * | 4/2003 | Ivri et al. ................. 239/102.2 |
| 6,543,443 B1 | 4/2003 | Klimowicz et al. |
| 6,546,927 B1 | 4/2003 | Litherland et al. |
| 6,550,472 B1 | 4/2003 | Litherland et al. |
| 6,554,201 B1 | 4/2003 | Klimowicz et al. |
| 6,615,824 B1 | 9/2003 | Power |
| 6,629,646 B1 | 10/2003 | Ivri |
| 6,640,804 B1 | 11/2003 | Ivri |
| 6,651,650 B1 | 11/2003 | Yamamoto et al. |
| 6,732,944 B1 | 5/2004 | Litherland et al. |
| 6,755,189 B1 | 6/2004 | Ivri et al. |
| 6,769,626 B1 | 8/2004 | Haveri |
| 6,782,886 B1 | 8/2004 | Narayan et al. |
| 6,814,071 B1 | 11/2004 | Klimowicz et al. |
| 6,845,770 B1 | 1/2005 | Klimowicz et al. |
| 6,851,626 B1 | 2/2005 | Patel et al. |
| 6,860,268 B1 | 3/2005 | Bohn et al. |
| 2001/0013554 A1 | 8/2001 | Borland et al. |
| 2001/0015737 A1 | 8/2001 | Truninger et al. |
| 2002/0011247 A1 | 1/2002 | Ivri et al. |
| 2002/0104530 A1 | 8/2002 | Ivri et al. |
| 2002/0121274 A1 | 9/2002 | Borland et al. |
| 2002/0134372 A1 | 9/2002 | Loeffler et al. |
| 2002/0134374 A1 | 9/2002 | Loeffler et al. |
| 2002/0134375 A1 | 9/2002 | Loeffler et al. |
| 2002/0134377 A1 | 9/2002 | Loeffler et al. |
| 2002/0162551 A1 | 11/2002 | Litherland |
| 2003/0140921 A1 | 7/2003 | Smith et al. |
| 2003/0150445 A1 | 8/2003 | Power et al. |
| 2003/0150446 A1 | 8/2003 | Patel et al. |
| 2003/0226906 A1 | 12/2003 | Ivri |
| 2004/0000598 A1 | 1/2004 | Ivri |
| 2004/0035490 A1 | 2/2004 | Power |
| 2004/0050947 A1 | 3/2004 | Power et al. |
| 2004/0139963 A1 | 7/2004 | Ivri et al. |
| 2004/0139968 A1 | 7/2004 | Loeffler et al. |
| 2004/0188534 A1 | 9/2004 | Litherland et al. |
| 2004/0256488 A1 | 12/2004 | Loeffler et al. |
| 2005/0011514 A1 | 1/2005 | Power et al. |

FOREIGN PATENT DOCUMENTS

| | | |
|---|---|---|
| CH | 555 681 | 11/1974 |
| EP | 0 049 636 A1 | 4/1982 |
| EP | 0 103 161 A2 | 3/1984 |
| EP | 0 134 847 A1 | 3/1985 |
| EP | 0 178 925 A2 | 4/1986 |
| EP | 0 387 222 A1 | 9/1990 |
| EP | 0 432 992 A1 | 6/1991 |
| EP | 0 476 991 B1 | 3/1992 |
| EP | 0 480 615 A1 | 4/1992 |
| EP | 0 510 648 A2 | 10/1992 |
| EP | 0 516 565 A1 | 12/1992 |
| EP | 0 542 723 A2 | 5/1993 |
| EP | 0 933 138 A2 | 4/1999 |
| EP | 0 923 957 A1 | 6/1999 |
| EP | 1 142 600 A1 | 10/2001 |
| FR | 2 692 569 | 12/1993 |
| GB | 973 458 | 10/1964 |
| GB | 1 454 597 | 11/1976 |
| GB | 2 073 616 A | 10/1981 |
| GB | 2 101 500 | 1/1983 |
| GB | 2 177 623 A | 1/1987 |
| GB | 2 240 494 A | 7/1991 |
| GB | 2 272 389 A | 5/1994 |
| GB | 2 279 571 A | 1/1995 |
| JP | 57-023852 | 2/1982 |
| JP | 57-105608 | 7/1982 |

| | | |
|---|---|---|
| JP | 58-061857 | 4/1983 |
| JP | 58-139757 | 8/1983 |
| JP | 59-142163 A | 8/1984 |
| JP | 60-004714 | 1/1985 |
| JP | 61-008357 A | 1/1986 |
| JP | 61-215059 A | 9/1986 |
| JP | 02-135169 | 5/1990 |
| JP | 02-189161 | 7/1990 |
| JP | 60-07721 A | 1/1994 |
| WO | WO 92/07600 A1 | 5/1992 |
| WO | WO 92/11050 A1 | 9/1992 |
| WO | WO 92/17231 A1 | 10/1992 |
| WO | WO 93/01404 A1 | 1/1993 |
| WO | WO 93/10910 A1 | 6/1993 |
| WO | WO 94/09912 A1 | 5/1994 |
| WO | WO 96/09229 | 3/1996 |
| WO | WO 99/17888 | 4/1999 |
| WO | WO 00/37132 | 6/2000 |

OTHER PUBLICATIONS

Allen, T. *Particle Size Measurement*, Third Edition, Chapman and Hall pp. 167-169 (1981).

Ashgriz, N. et al. "Development of a Controlled Spray Generator" Rev. Sci. Instrum., 1987, pp. 1291-1296, vol. 58, No. 7.

Berglund, R.N., et al. "Generation of Monodisperse Aerosol Standards" Environ. Sci. Technology, Feb. 1973, pp. 147-153, vol. 7, No. 2.

Gaiser Tool Company catalog, pp. 26, 29-30 (1990).

Heyder, J. et al., "Deposition of particles in the human respiratory tract in the size range 0.005-15 microns." J Aerosol Sci 17:811-825, 1986.

Hickey, Anthony J. "Pharmaceutical Inhalation Aerosol Technology," Drugs And The Pharmaceutical Science, 1992, pp. 172-173, vol. 54.

Hikayama, H., et al. "Ultrasonic Atomizer with Pump Function" Tech. Rpt. IEICE Japan US88-74:25 (1988).

Maehara, N. et al. "Atomizing rate control of a multi-pinhole-plate ultrasonic atomizer" J. Acoustical Soc. Japan, 1988, pp. 116-121, 44:2.

Maehara, N. et al. "Influence of the vibrating system of a multipinhole-plate ultrasonic nebulizer on its performance" Review of Scientific Instruments, Nov. 1986, p. 2870-2876, vol. 57, No. 1.

Maehara, N. et al. "Influences of liquid's physical properties on the characteristics of a multi-pinhole-plate ultrasonic atomizer" J. Acoustical Soc. Japan 1988, pp. 425-431, 44:6.

Maehara, N. et al. "Optimum Design Procedure for Multi-Pinhole-Plate Ultrasonic Atomizer" Japanese Journal of Applied Physics, 1987, pp. 215-217, vol. 26, Supplement 26-1.

Nogi, T. et al. "Mixture Formation of Fuel Injection System in Gasoline Engine" Nippon Kikai Gakkai Zenkoku Taikai Koenkai Koen Ronbunshu 69:660-662 (1991).

Palla Tech Pd an Pd Alloy Processes-Procedure for the Analysis of Additive IVS in Palla Tech Plating Solutions by HPLC, Technical Bulletin, Electroplating Chemicals & Services, 029-A, Lucent Technologies,, pp. 1-5, 1996.

SIEMENS, "Servo Ultra Nebulizer 345 Operating Manual," pp. 1-23.

TSI Incorporated product catalog. Vibrating Orifice Aerosol Generator (1989).

Ueha, S., et al. "Mechanism of Ultrasonic Atomization Using a Multi-Pinhole Plate" J. Acoust. Soc. Jpn., 1985, pp. 21-26, (E)6,1.

Wehl, Wolfgang R. "Ink-Jet Printing: The Present State of the Art" for Siemens AG, 1989.

* cited by examiner

SYSTEMS AND METHODS FOR CONTROLLING FLUID FEED TO AN AEROSOL GENERATOR

CROSS-REFERENCES TO RELATED APPLICATIONS

This application is a continuation application of U.S. patent application Ser. No. 09/678,410, filed Oct. 2, 2000 (now U.S. Pat. No. 6,540,154), which is a continuation-in-part application of U.S. patent application Ser. No. 09/318,552, filed May 27, 1999, now U.S. Pat. No. 6,540,153 which is a continuation application of U.S. patent application Ser. No. 08/417,311, filed Apr. 5, 1995 (now U.S. Pat. No. 5,938,117), which is a continuation-in-part application of U.S. patent application Ser. No. 08/163,850 filed on Dec. 7, 1993, now U.S. Pat. No. 6,629,646 which is a continuation-in-part of U.S. patent application Ser. No. 07/726,777 filed on Jul. 8, 1991 (now abandoned), which is a continuation-in-part of U.S. patent application Ser. No. 07/691,584 filed on Apr. 24, 1991, now U.S. Pat. No. 5,164,740. The complete disclosures of all these references are herein incorporated by reference.

BACKGROUND OF THE INVENTION

The present invention relates to improved aerosolizing devices, particularly but not exclusively for atomizing liquid medicaments to be inhaled, and to a method of constructing such devices.

A wide variety of procedures have been proposed to deliver a drug to a patient. Of particular interest to the present invention are drug delivery procedures where the drug is a liquid and is dispensed in the form of fine liquid droplets for inhalation by a patient. A variety of devices have been proposed for forming the dispersion, including air jet nebulizers, ultrasonic nebulizers and metered dose inhalers (MDIs). Air jet nebulizers usually utilize a high pressure air compressor and a baffle system that separates the large particles from the spray. Ultrasonic nebulizers generate ultrasonic waves with an oscillating piezoelectric crystal to produce liquid droplets. Another type of ultrasonic nebulizer is described in U.S. Pat. Nos. 5,261,601 and 4,533,082. Typical MDIs usually employ a gas propellant, such as a CFC, which carries the therapeutic substance and is sprayed into the mouth of the patient.

The present applicant has also proposed a variety of aerosolization devices for atomizing liquid solutions. For example, one exemplary atomization apparatus is described in U.S. Pat. No. 5,164,740, the complete disclosure of which is herein incorporated by reference. The atomization apparatus comprises an ultrasonic transducer and an aperture plate attached to the transducer. The aperture plate includes tapered apertures which are employed to produce small liquid droplets. The transducer vibrates the plate at relatively high frequencies so that when the liquid is placed in contact with the rear surface of the aperture plate and the plate is vibrated, liquid droplets will be ejected through the apertures. The apparatus described in U.S. Pat. No. 5,164,740 has been instrumental in producing small liquid droplets without the need for placing a fluidic chamber in contact with the aperture plate. Instead, small volumes of liquid are delivered to the rear surface of the aperture plate and held in place by surface tension forces.

Modified atomization apparatus are described in U.S. Pat. Nos. 5,586,550 and 5,758,637, the complete disclosures of which are herein incorporated by reference. The two references describe a liquid droplet generator which is particularly useful in producing a high flow of droplets in, a narrow size distribution. As described in U.S. Pat. No. 5,586,550, the use of a dome shaped aperture plate is advantageous in allowing more of the apertures to eject liquid droplets.

One requirement of such aerosolization devices is the need to supply liquid to the aperture plate. In some applications, such as when delivering aerosolized medicaments to the lungs, it may be desirable to regulate the supply of the liquid to the aperture plate so that proper pulmonary delivery of the drug may occur. For example, if too much liquid is supplied, the aerosol generator may be unable to aerosolize fully all of the delivered liquid. On the other hand, if too little liquid is supplied, the user may not receive a sufficient dosage. Further, a metering process may be needed to ensure that a unit dosage amount of the liquid is delivered to the aerosol generator. This may be challenging if the user requires several inhalations in order to inhale the unit dose amount.

The present invention is related to liquid feed systems and methods for delivering liquids to the aerosol generator to facilitate aerosolization of the liquid.

SUMMARY OF THE INVENTION

The invention provides exemplary aerosolization devices and methods for aerosolizing liquids. In one embodiment, an aerosolization device comprises a liquid supply system that is adapted to hold a supply of liquid, and an aerosol generator that is configured to aerosolize liquid supplied from the liquid supply system. In one aspect, the aerosol generator may comprise a plate having a plurality of apertures and a vibratable element disposed to vibrate the plate. The aerosolization device further comprises a sensor configured to sense an amount of unaerosolized liquid supplied to the aerosol generator, and a controller to control operation of the liquid supply system based on information received from the sensor. In this way, during aerosolization the amount of unaerosolized liquid supplied to the aerosol generator remains within a certain range. In this manner, the device is configured to prevent either too much or too little liquid from being supplied to the aerosol generator at any one time.

In one aspect, the sensor comprises a strain gauge coupled to the aerosol generator for detecting variations in strain caused by varying amounts of unaerosolized liquid adhering to the aerosol generator. The strain gauge may comprise a piezoelectric element coupled to the aerosol generator such that variations in an electrical characteristic (e.g. impedance) are representative of unaerosolized liquid adhering to the aerosol generator. The piezoelectric element may also act as a transducer disposed to vibrate an aperture plate in the aerosol generator.

In another aspect, the sensor may comprise an optical sensor. The optical sensor may be configured to sense the presence or absence of unaerosolized liquid at a certain location on the aerosol generator. The certain location may be spaced from where liquid is supplied to the aerosol generator.

In yet another aspect, the sensor may be a conductivity sensor that is configured to sense electrical conductivity between at least two points across a surface of the aerosol generator on which unaerosolized liquid may adhere. At least one of the points may be spaced from where liquid is supplied to the aerosol generator. Further, at least one of the points may be closer to where liquid is supplied to the aerosol generator than another one of the points. In this way, sensing electrical conductivity may give an indication of unaerosolized liquid distribution across the aerosol generator.

In one particular embodiment, the amount of unaerosolized liquid on the aerosol generator remains within the range from about 0 to about 20 microliters, and more preferably from about 2 microliters to about 20 microliters.

The device may further comprise a housing having a mouthpiece, with the aerosol generator disposed in the housing for delivery of aerosolized liquid through the mouthpiece. In this way, a drug may be aerosolized and ready for pulmonary delivery upon patient inhalation.

In another particular aspect, the liquid supply system may comprise a dispenser for dispensing a certain amount of liquid upon receipt of an appropriate signal from the controller. In this way, a predetermined amount of liquid may be chosen to ensure the aerosol generator is not overloaded at any one time. The device may further comprise a meter for limiting the number of times the dispenser is activated during operation of the aerosol generator. In this way, the total liquid delivered by the aerosol generator in any one period of operation may be accurately controlled, thereby limiting the risk of delivering below or above a recommended dose.

In yet another particular embodiment, the device may further comprise a heater for heating unaerosolized liquid supplied to the aerosol generator. The heater may be adapted to heat the aerosol generator to vaporize or burn off residual unaerosolized liquid after aerosol generator cessation. In this way, residual unaerosolized liquid may be removed to prevent interference with a subsequent aerosolization event. The heater may comprise an electrical resistance heater and an electrical power supply (e.g. battery) for energizing resistance heating.

In another embodiment of the invention, a method for aerosolizing a liquid utilizes an aerosol generator that is operable to aerosolize a liquid. According to the method, a liquid is supplied to the aerosol generator from a liquid supply system at an initial flow rate. During aerosolization, the amount of supplied liquid remaining unaerosolized is sensed and the rate of liquid supply regulated based upon the sensed amount. The rate of liquid supply may be decreased if the sensed amount exceeds a certain value, and the rate of liquid supply may be increased if the sensed amount falls below a critical level. In this way, it is possible to prevent or to reduce the extent of supplying too much or too little liquid being supplied to the aerosol generator at any one time.

In one aspect, the method further comprises providing a heater for heating unaerosolized liquid supplied to the aerosol generator. By sensing whether any of the supplied liquid remains unaerosolized after cessation of the liquid supply, the heater may be operated to vaporize or burn-off such supplied liquid remaining on the aerosol generator.

In yet another embodiment of the invention, an aerosolization device comprises a liquid supply system that is adapted to hold a supply of liquid, and an aerosol generator comprising a plate having a plurality of apertures and an electric transducer disposed to vibrate the plate when energized. A sensor is configured to sense an electrical characteristic of the electrical transducer that is dependent upon an amount of unaerosolized liquid adhering to the plate. A controller is provided to regulate operation of the liquid supply in order to maintain the amount of unaerosolized liquid adhering to the plate within a certain range during aerosolization.

In a still further embodiment, a method is provided for controlling the supply of a liquid to an aerosol generator. According to the method, a liquid supply system is operated to supply a liquid to a vibratable aperture plate of an aerosol generator. An amount of liquid adhering to the vibratable plate is sensed and is used to control the amount of liquid supplied to the plate. By controlling operation of the liquid supply system, the amount of liquid adhering to the vibratable aperture plate may be regulated.

DESCRIPTION OF THE SPECIFIC EMBODIMENTS

The invention provides exemplary aerosolization devices and methods for controlling the supply of a liquid to an aerosol generator. The invention is applicable to essentially any aerosolizer where liquid delivered to the aerosolizer may accumulate leading to variation in device performance. Merely by way of example, the invention may be used with atomizers such as those described in U.S. Pat. Nos. 5,140,740, 5,938,117, 5,586,550, and 6,014,970, incorporated herein by reference. However, it will be appreciated that the invention is not intended to be limited only to these specific atomizers.

Aerosolization devices embodying the present invention conveniently sense the amount of unaerosolized liquid which has accumulated at the aerosol generator. This information is used to modify the rate of supply of liquid to the aerosol generator to maintain the amount of liquid adhering to the aerosol generator within certain limits. In this way, the aerosol generator is neither oversupplied nor under supplied with liquid, and is able to operate efficiently and effectively.

The sensor may take a variety of forms. For example, the sensor may be a piezoelectric device for sensing strains induced on the aerosol generator by liquid loads. Alternatively, the sensor may be an optical sensor, a conductivity sensor, or the like for sensing amounts of unaerosolized liquid on the aerosol generator. Another feature is the potential ability to vaporize or burn off unwanted unaerosolized liquid from the aerosol generator. The requisite heat may be applied by an electrical resistance heater, or the like.

In one embodiment, the supply of liquid to the aerosol generator is delivered in predetermined quantities. Each predetermined quantity may be a fraction of a total dose, and thus each delivery of the predetermined delivery may be counted. When the number of deliveries matches the quantity of the total dose, the liquid supply is interrupted.

Figure 1:
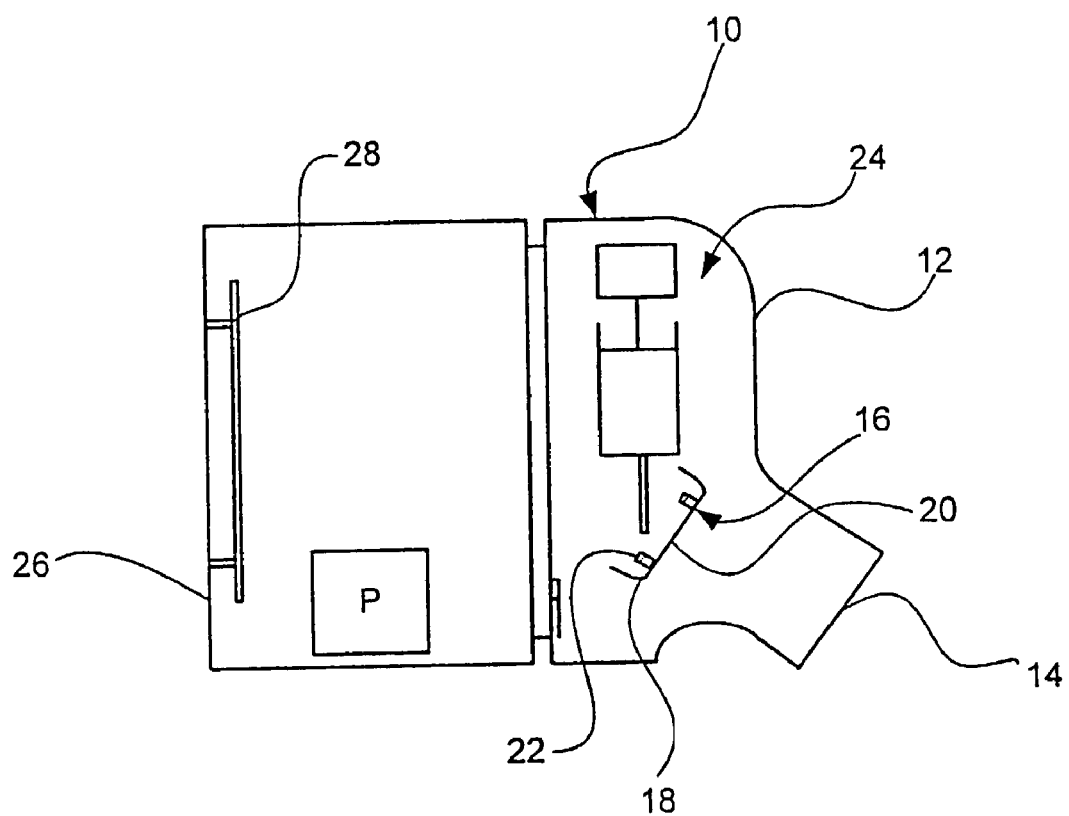
FIG. 1 is a cross-sectional schematic diagram of an aerosolization device according to the invention.
Figure 8:
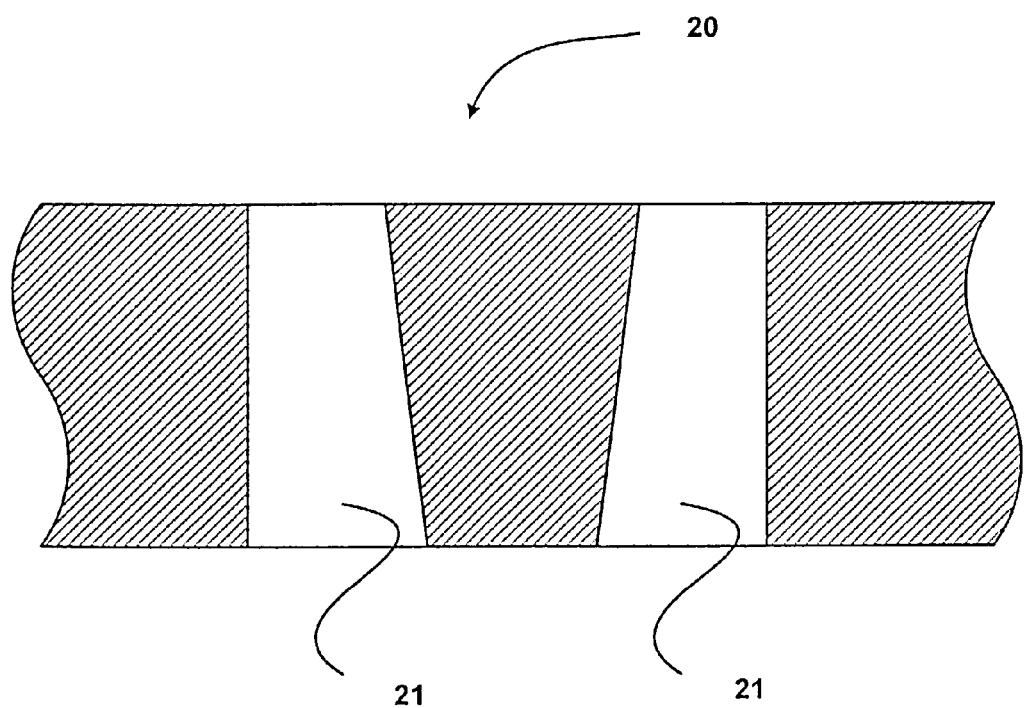
FIG. 8 is a cross-sectional diagram of an aperature plate according to one embodiment of the invention.

Referring now to FIG. 1, one embodiment of an aerosolization device 10 will be described. Device 10 comprises a housing 12 to hold the various components of aerosolization device 10. Housing 12 further includes a mouthpiece 14 and one or more vents (not shown) to permit air to enter into housing 12 when a user inhales from mouthpiece 14. Disposed within housing 12 is an aerosol generator 16 that comprises a cup-shaped member 18 to which is coupled an aperture plate 20. An annular piezoelectric element 22 is in contact with aperture plate 20 to cause aperture plate 20 to vibrate when electrical current is supplied to piezoelectric element 22. Aperture plate 20 is dome-shaped in geometry and, as shown in FIG. 8, includes a plurality of tapered apertures 21 that narrow from the rear surface to the front surface. Exemplary aperture plates and aerosol generators that may be used in aerosolization device 10 are described in U.S. Pat. Nos. 5,086,785, 5,157,372 and 5,309,135, incorporated herein by reference.

Aerosolization device 10 further includes a liquid feed system 24 having a supply of liquid that is to be aerosolized by aerosol generator 16. Liquid feed system 24 may be configured to place metered amounts of liquid onto aperture plate 20. Although not shown, a button or the like may be employed to dispense the liquid when requested by the user. Conveniently, feed system 24 may be configured to supply a unit dose of liquid over time to aperture plate 20. As described hereinafter, a variety of sensors may be used to monitor and control the amount of liquid supplied to aperture plate 20 so that the amount of unaerosolized liquid remains within a certain range.

Housing 12 includes an electronics region 26 for holding the various electrical components of aerosolization device 10. For example, region 26 may include a printed circuit board 28 which serves as a controller to control operation of the aerosol generator 16. More specifically, circuit board 28 may send (via circuitry not shown) an electrical signal to piezoelectric element 22 to cause aperture plate 20 to be vibrated. A power supply P, such as one or more batteries, is electrically coupled to circuit board 28 to provide aerosolization device 10 with power. Optionally, a flow sensor may be used to sense patient inhalation and to operate aerosol generator 16 only when a threshold flow rate has been produced by the user. One example of such a flow sensor is described in copending U.S. patent application Ser. No. 09/149,246, filed Sep. 8, 1998, the complete disclosure of which is herein incorporated by reference.

Figure 2:
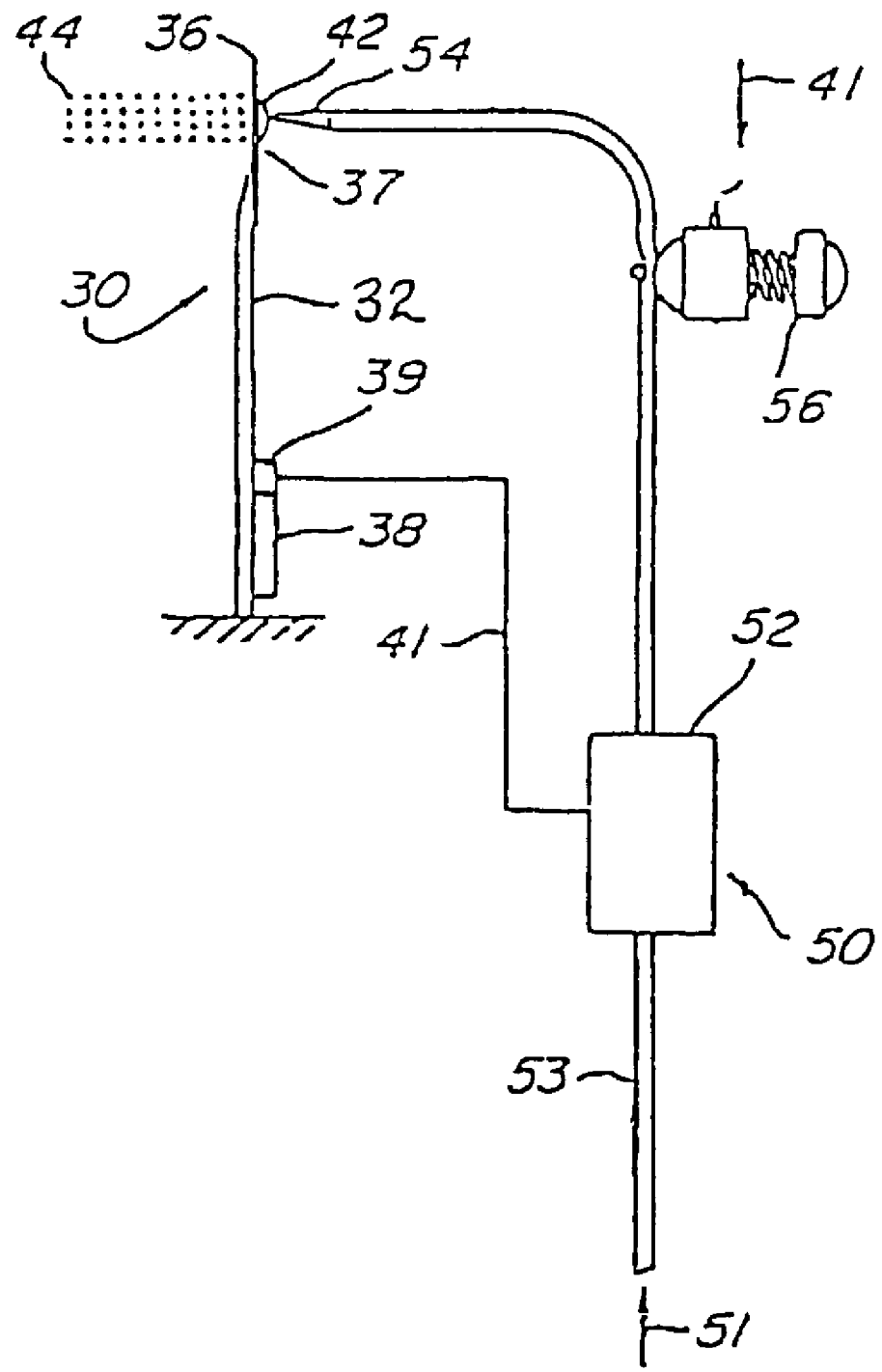
FIG. 2 is a schematic diagram showing an alternative aerosolization device and liquid supply system embodying the present invention.

FIG. 2 illustrates schematically an alternative aerosol generator 30 with one fluid supply system according to an embodiment of the invention. The fluid supply system is configured to maintain a proper supply of liquid to aerosol generator 30. Although described in connection with aerosol generator 30, it will be appreciated that the system of FIG. 2 may be used with any of the aerosolization devices described herein.

The aerosol generator 30 is in the form of a cantilevered beam 32 on which a piezoelectric oscillator 38 is mounted. The free end 37 of the beam 32 is provided with a planar surface through which there are microscopic tapered apertures. Fluid 42 in contact with the free end 37 is ejected through the tapered apertures producing droplets 44 when the beam is oscillated at high frequency by the piezoelectric oscillator 38. The fluid supply system 50 continuously transports fluid 51 to wet the oscillating surface 37 via a supply tube 53 ending at a supply nozzle 54. The fluid 51 is transported to the surface 37 at a rate which is lower than the maximum ejection rate of the apertures 40 to prevent overflow of fluid 42 from the supply side of the oscillating surface 37. A pinch valve 56 controls delivery of the fluid 51 to the oscillating surface 37. The fluid supply system 50 is connected to an electronic flow control valve 52 which is connected to an electronic circuit that detects the amount of liquid 42 on the oscillating surface 37. In the event of excessive delivery of fluid, the oscillation amplitude decreases and the current draw by the piezoelectric element 38 decreases. This is because as the load changes, there is a corresponding change in the impedance of the piezoelectric element. A current sensor circuit 39 senses the current draw and transmits an overflow signal 41 to the flow control valve 52 to reduce the delivery rate of the liquid 51 to the surface 37 until the amount of fluid returns to normal level.

The arrangement described in FIG. 2 utilizes an electrical characteristic (e.g. impedance) of the piezoelectric element 38 which is dependent upon the liquid load on aerosol generator 30. By sensing the electrical characteristic, either in absolute or relative terms, it is possible to control the rate of liquid supply to the aerosol generator in order to maintain the amount of unaerosolized liquid adhering to the beam 32 within certain limits. In other words, if the amount of unaerosolized liquid on the beam 32 falls below a lower limit, the flow rate may be increased to prevent the aerosol generator from running dry. On the other hand, if the amount of unaerosolized liquid on the beam 32 rises above an upper limit, the flow rate may be decreased or even temporarily suspended to prevent overloading of the aerosol generator. As previously mentioned, such a system may also be used with aerosol generator 16 of FIG. 1 by sensing the amount drawn by piezoelectric element 22.

Figure 3:
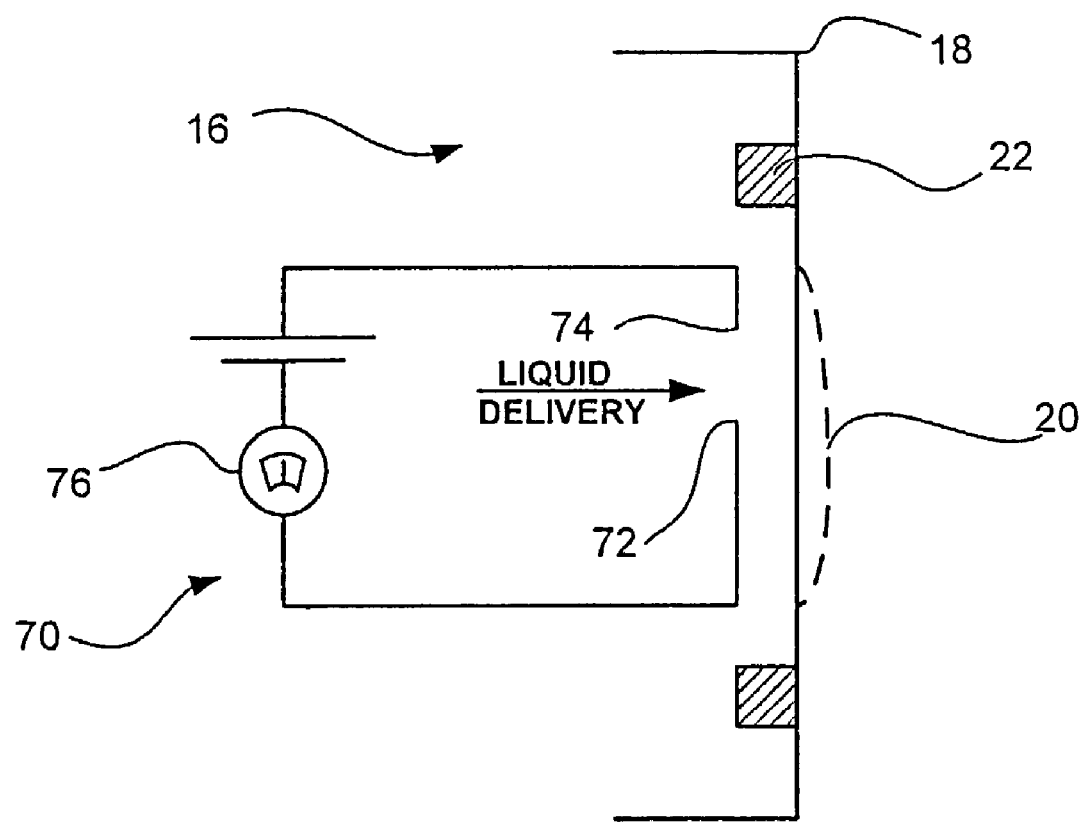
FIG. 3 is a schematic diagram of one embodiment of a fluid sensor according to the invention.

FIG. 3 schematically illustrates a conductive sensor 70 that may be used to sense the volume of fluid on an aperture plate, including any of those described herein. For convenience of discussion, sensor 70 is described with reference to aerosol generator 18 of FIG. 1. Conductive sensor 70 is used to measure electrical conductivity between two points 72,74 above a surface of aperture plate 20 to which unaerosolized liquid adheres. One of the points 72 is located adjacent where liquid is delivered to the aerosol generator, while the other point 74 is spaced laterally of where such liquid is delivered. In use, a build-up of unaerosolized liquid on aperture plate 20 will have no appreciable effect on electrical conductivity measured by a detector 76, until the unaerosolized liquid bridges the spacing between point 72,74. When the detector 76 registers a sudden change in conductivity—indicative of current flowing through unaerosolized liquid—the flow rate of liquid supply may be reduced to avoid further build-up of liquid. A second conductive sensor (not shown) may be positioned to detect when the amount of unaerosolized liquid falls below a lower level, for triggering an increase in liquid flow when required. In this way, conductivity may be used to maintain the amount of unaerosolized liquid supplied to the aerosol generator within certain limits.

In another embodiment, the conductive sensor 70 may be replaced with an optical sensor which, for example, senses the present or absence of unaerosolized liquid in a certain location, or series of discrete locations on the aperture plate. If the presence of unaerosolized liquid is sensed at an outer location spaced from the point of liquid delivery to the aerosol generator, the flow rate of liquid supply may be reduced. If the absence of unaerosolized liquid is sensed in another location spaced inwardly from the outer location, the flow rate of liquid supply may be increased.

Figure 4:
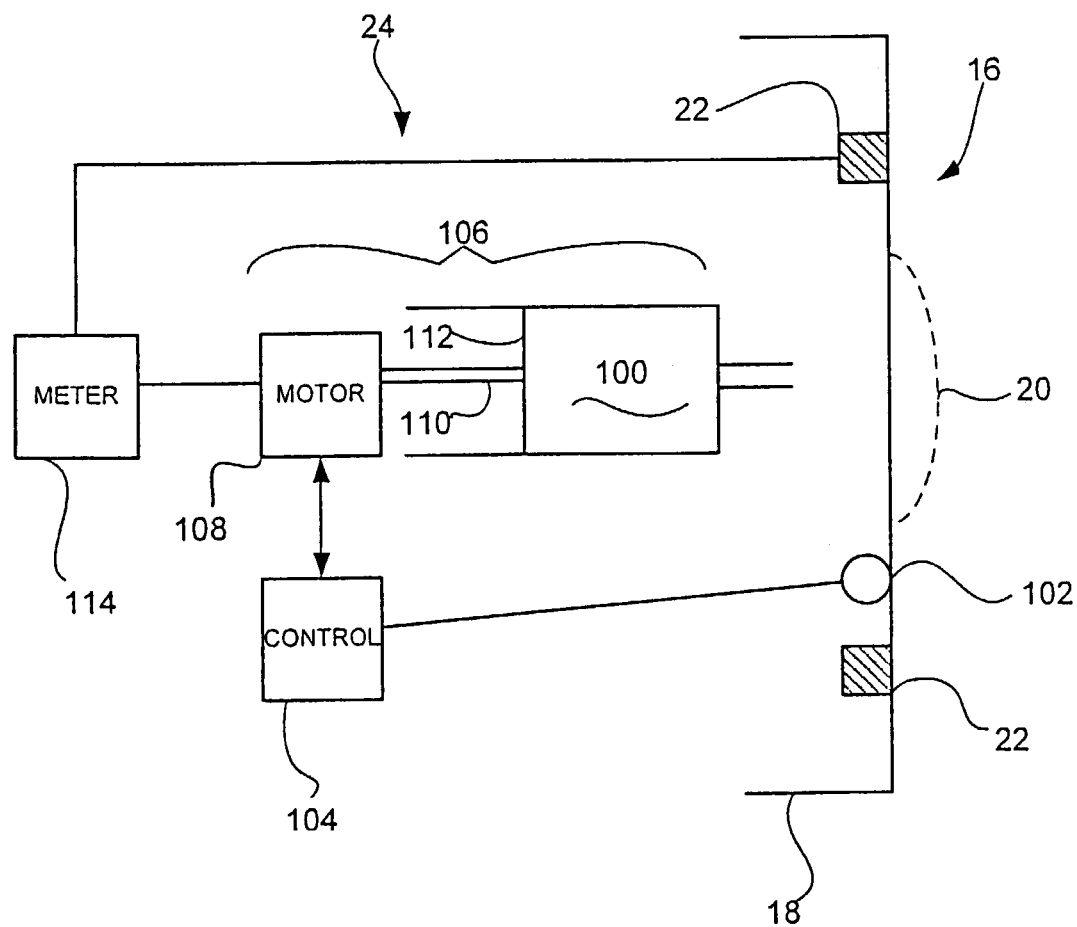
FIG. 4 is a schematic diagram of one embodiment of a liquid supply system according to the invention.
Figure 7:
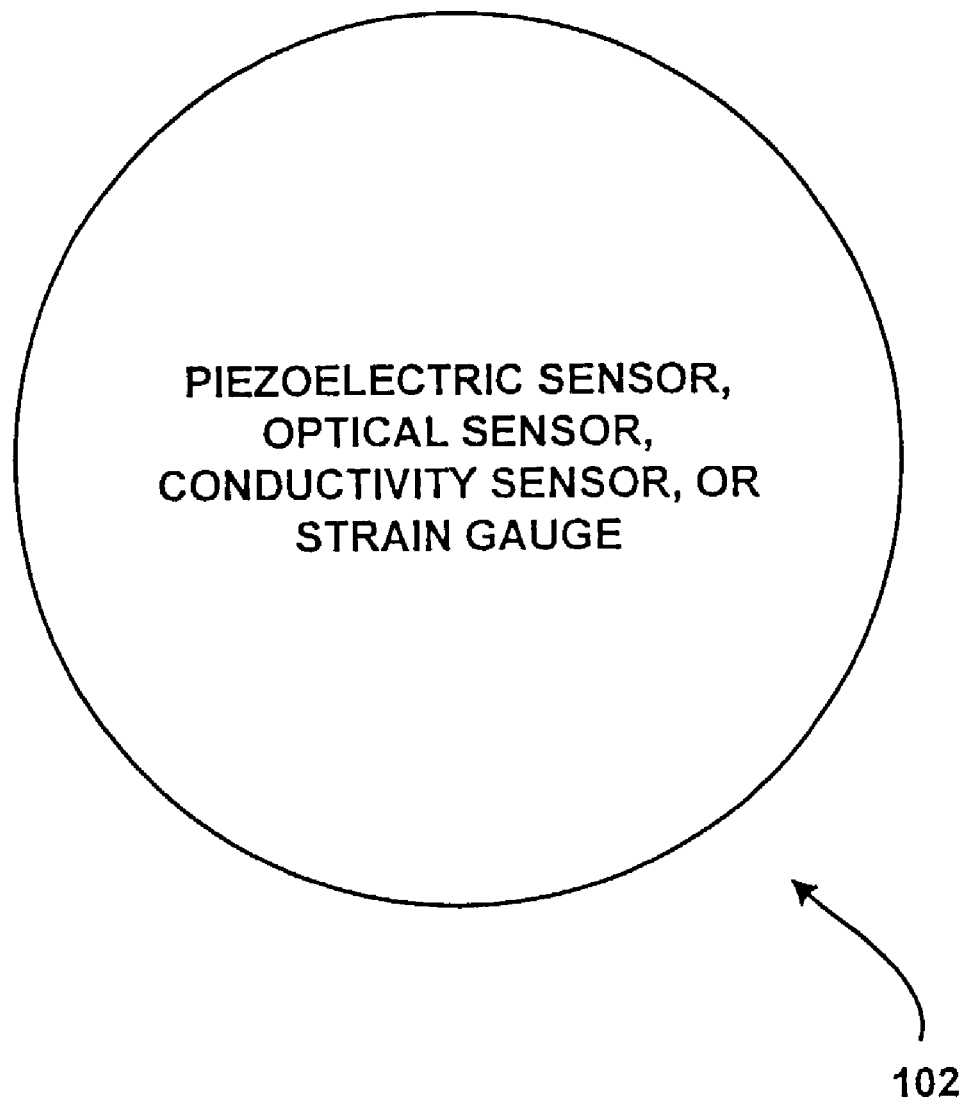
FIG. 7 is a drawing illustrating several embodiments of a fluid sensor according to the invention.

FIG. 4 schematically illustrates in more detail liquid feed system 24 of FIG. 1. Liquid feed system 24 includes a canister 100 configured to deliver liquid to aperture plate 20 of aerosol generator 16. A sensor 102 (which, as shown in FIG. 7, may be a strain or may be a piezo, conductive or optical sensor) senses the unaerosolized liquid adhering to the aperture plate 20, and relays this information to controller 104. Controller 104 controls a dispensing system 106 which, upon receipt of dispensed signal from controller 104, dispenses a predetermined amount of liquid (e.g. 5 microliters) from canister 100. Dispensing system 106 comprises a motor 108 which drives a lead screw 110 coupled to a piston 112 associated with canister 100. When the controller 104 senses via sensor 102 that the amount of unaerosolized liquid on the aperture plate 20 has fallen below a lower limit, it activates motor 108 for a predetermined time, e.g. one second. In this time, motor 108 turns lead screw 110 causing piston 112 to advance a predetermined amount and hence deliver a measured quantity of liquid to the aerosol generator.

A meter 114 is coupled to the motor 108 and to the piezoelectric transducer 22. The meter 114 counts the number of times the motor 108 is activated in any period of continuous operation of the aerosol generator, i.e., while piezoelectric transducer 22 is vibrating. The meter 114 serves to prevent the motor 108 from being operated more than a predetermined number of times (e.g., 20) in any one period of use. In this way, the user may continue to use the aerosol generator 16 until an appropriate dose has been aerosolized (e.g., 20×5 microliters=100 microliters). At this time, operation of the motor 108 is temporarily stopped by the meter 114 and a corresponding signal sent to controller 104. Such a signal may enable an indication to be given to the user that a full dose has been delivered.

In some cases, the user may stop operation without aerosolizing the full dose. The controller may be configured to record the partial dosage and notify the user when attempting to continue operation.

Figure 5:
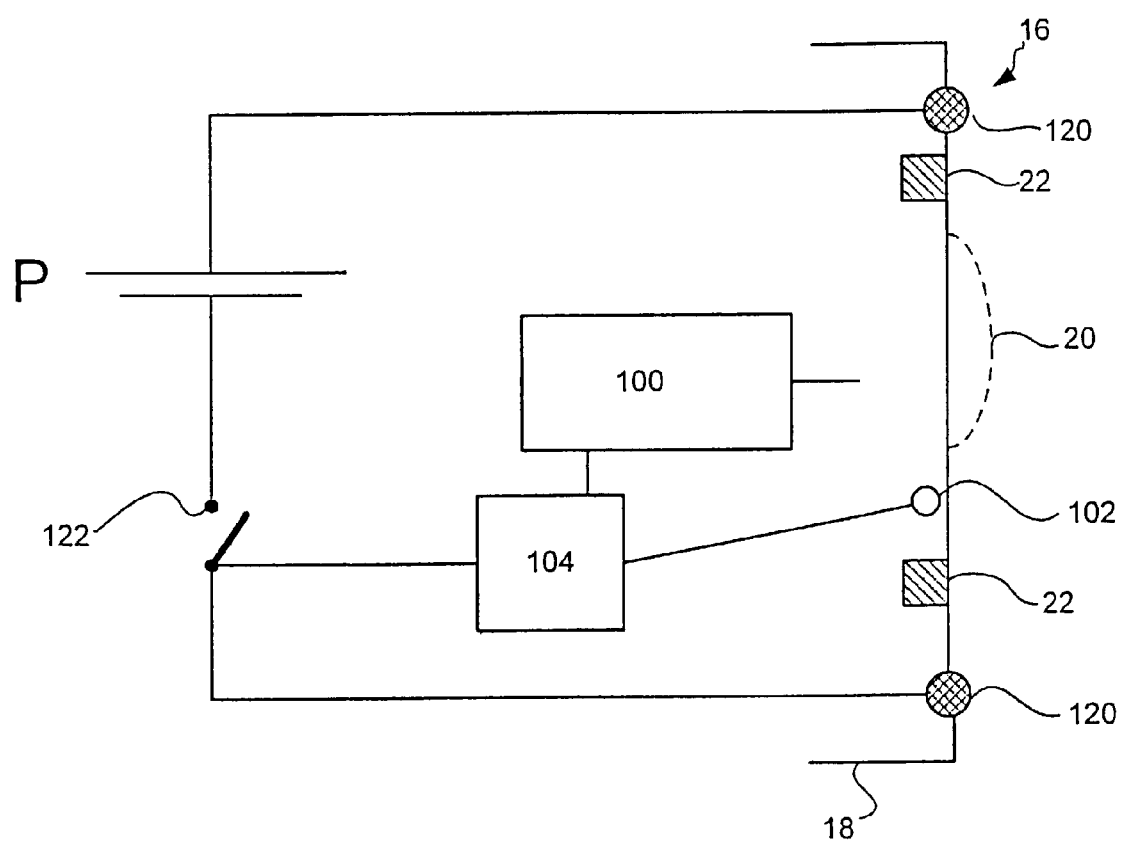
FIG. 5 is a schematic diagram showing a heater for an aerosol generator according to the invention.

FIG. 5 schematically illustrates a heater 120 for an aerosol generator, such as aerosol generator 16 of FIG. 1. Heater 120 is useful when unaerosolized liquid remains on the aperture plate 20 after the supply of liquid has ceased, e.g., because required dose has been delivered or the user stops operation. Heater 120 is incorporated into the aerosol generator 16 in order to vaporize or burn off excess unaerosolized liquid on the aperture plate 20. Heater 120 is an annular electrical resistance heater, and is energized by power source P under control of controller 104. In use, sensor 102 relays information to the controller 104 that unaerosolized liquid remains on the aperture plate 20 after the supply of liquid through supply system 100 has ceased. If this situation remains unchanged for a predetermined time interval, the controller 104 may activate switch 122 to heat aperture plate 20 by heater 120. In this way, excess unaerosolized liquid may be removed, ensuring the aperture plate 20 is clear and ready for reuse.

Figure 6:
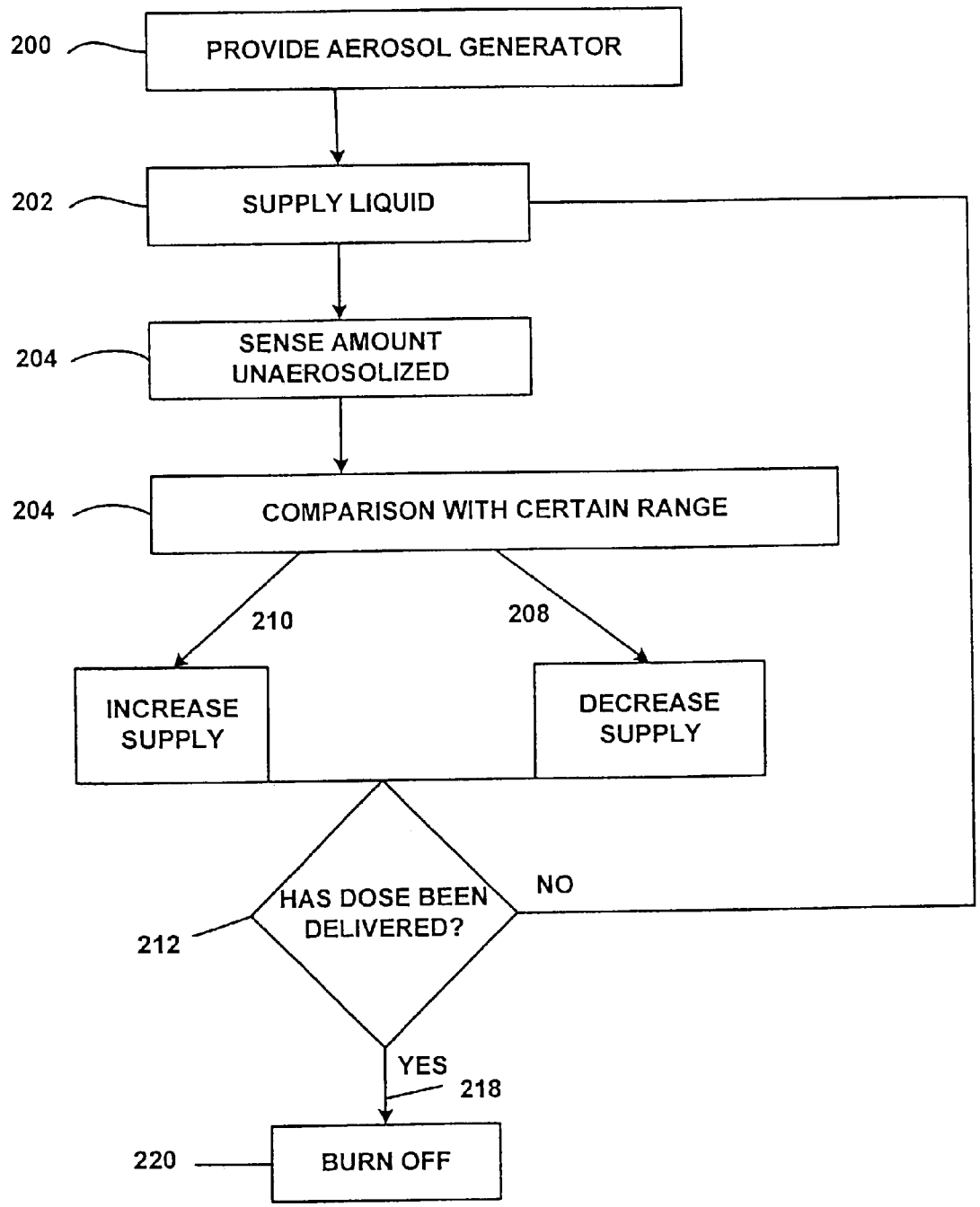
FIG. 6 is a flow chart illustrating one method of controlling the supply of liquid to an aerosol generator.

Referring now to FIG. 6, one method of controlling the supply of liquid to an aerosolizing device will now be described. The process begins at step 200 where an aerosol generator is provided. Liquid is supplied at step 202 to the aerosol generator for aerosolization. Some of the liquid supplied is unaerosolized and accumulates on the aerosol generator, and the amount of such liquid is sensed as shown at step 204. The amount of liquid sensed is then compared at step 206 with a predetermined range of amounts, the upper limit of which corresponds to the maximum desired amount on the aerosol generator, and the lower limit of which corresponds to the minimum desired amount on the aerosol generator. If the sensed amount exceeds the upper limit, the flow rate is decreased at step 208, and if the sensed amount falls below the lower limit, the flow rate is increased as shown at step 210. The total amount of liquid supplied to the aerosol generator is monitored at step 212. If the total amount is less than a predetermined total dose, the supply cycle is repeated, and if the total amount is equal to the predetermined dose, the supply is terminated at step 218. Any unaerosolized liquid on the aerosol generator after terminating the supply is burnt off at 220 by energizing an electric heater.

The invention has now been described in detail for purposes of clarity of understanding. However, it will be appreciated that certain changes and modifications may be practiced within the scope of the appended claims.

What is claimed is:

1. An aerosolization device comprising:
   a liquid supply system that is adapted to hold a supply of liquid;
   an aerosol generator configured to aerosolize liquid supplied from the liquid supply system;
   a sensor that is configured to sense an amount of unaerosolized liquid that has been previously supplied to the aerosol generator; and
   a controller to control operation of the liquid supply system based on information received from the sensor.

2. An aerosolization device according to claim 1, wherein the aerosol generator comprises a vibratable element and an aperture plate.

3. An aerosolization device according to claim 2, wherein the aperture plate includes a plurality of tapered apertures.

4. An aerosolization device according to claim 1, wherein the controller is configured to maintain the amount of supplied and unaerosolized liquid within a certain range during aerosolization.

5. An aerosolization device according to claim 1, wherein the sensor comprises a strain gauge coupled to the aerosol generator for detecting variations in strain according to variations in the amount of unaerosolized liquid in contact with the aerosol generator.

6. An aerosolization device according to claim 5, wherein the strain gauge comprises a piezoelectric element, with variations in the amount of unaerosolized liquid adhered to the aerosol generator causing corresponding variations in an electrical characteristic of the piezoelectric element.

7. An aerosolization device according to claim 6, further comprising electrical circuitry configured to measure variations in impedance of the piezoelectric element.

8. An aerosolization device according to claim 6, wherein the piezoelectric element is disposed to vibrate an aperture plate in the aerosol generator.

9. An aerosolization device according to claim 1, wherein the sensor comprises an optical sensor.

10. An aerosolization device according to claim 9, wherein the optical sensor is configured to sense the presence or absence of supplied and unaerosolized liquid in a certain location on the aerosol generator.

11. An aerosolization device according to claim 10, wherein the certain location is spaced from where liquid is supplied to the aerosol generator.

12. An aerosolization device according to claim 1, wherein the sensor comprises a conductive sensor configured to sense electrical conductivity between at least two points across a surface of the aerosol generator on which supplied and unaerosolized liquid adheres, at least one point being spaced from where liquid is supplied to the aerosol generator.

13. An aerosolization device according to claim 12, wherein one of the at least two points is closer to where liquid is supplied to the aerosol generator than another of the at least two points.

14. An aerosolization device according to claim 1, wherein the amount of unaerosolized liquid supplied to the aerosol generator remains within the range from about 2 to about 20 ÿl (microliters).

15. An aerosolization device according to claim 1, further comprising a housing having a mouthpiece, the aerosol generator being disposed in the housing for delivery of aerosolized liquid through the mouthpiece.

16. An aerosolization device according to claim 1, wherein the liquid supply system comprises a dispenser for dispensing a certain amount of liquid upon receipt of a dispense signal from the controller.

17. An aerosolization device according to claim 16, further comprising a meter for limiting the number of times the dispenser is activated during operation of the aerosol generator.

18. An aerosolization device according to claim 1, further comprising a heater for heating unaerosolized liquid supplied to the aerosol generator.

19. An aerosolization device according to claim 18, wherein the heater is configured to heat the aerosol generator to vaporize the unaerosolized liquid.

20. An aerosolization device according to claim 19, wherein the heater comprises an electrical resistance heating element and an electrical power supply for energizing resistance heating.

21. An aerosolization device comprising:
a liquid supply system that is adapted to hold a supply of liquid;
an aerosol generator comprising an element having a plurality of apertures and an electrical transducer disposed to vibrate the element when energized;
a sensor configured to sense an electrical characteristic of the electrical transducer that is dependent upon an amount of unaerosolized liquid adhering to the element; and
a controller to control operation of the liquid supply system based on the electrical characteristic sensed by the sensor, whereby the amount of unaerosolized liquid adhering to the element is maintained within a certain range during aerosolization.

22. An aerosolization device according to claim 21, wherein the electrical transducer comprises a piezoelectric element.

23. An aerosolization device according to claim 22, wherein the electrical characteristic sensed by the sensor is the impedance of the piezoelectric element.

24. An aerosolization device according to claim 21, wherein the controller is configured to maintain the amount of unaerosolized liquid adhering to the element within a range of from about 2 to about 20 ÿl (microliters) during aerosolization.

25. An aerosolization device according to claim 21, further comprising a housing having a mouthpiece, the aerosol generator being disposed in the housing for delivery of aerosolized liquid through the mouthpiece.

26. An aerosolization device according to claim 21, wherein the liquid supply system comprises a dispenser for dispensing a certain amount of liquid upon receipt of a dispense signal from the controller.

27. An aerosolization device according to claim 26, further comprising a meter for limiting the number of times the dispenser dispenses the amount of liquid during operation of the aerosol generator.

28. An aerosolization device according to claim 21, further comprising a heater for heating unaerosolized liquid supplied to the aerosol generator.

29. An aerosolization device according to claim 28, wherein the heater is adapted to heat the aerosol generator to vaporize the unaerosolized liquid applied to the aerosol generator.

* * * * *